United States Patent [19]

Owen

[11] 4,351,899

[45] Sep. 28, 1982

[54] SEMI-QUANTITATIVE ASSAY OF METABOLIC ACIDS

[76] Inventor: Oliver E. Owen, 1401 Spring Mill Rd., Gladwyne, Pa. 19035

[21] Appl. No.: 235,776

[22] Filed: Feb. 19, 1981

Related U.S. Application Data

[63] Continuation-in-part of Ser. No. 925,946, Jul. 19, 1978, Pat. No. 4,254,222.

[51] Int. Cl.³ ............................................. C12Q 1/32
[52] U.S. Cl. ...................................... 435/26; 435/805; 435/810
[58] Field of Search .................... 435/26, 805, 810

[56] References Cited

U.S. PATENT DOCUMENTS

| | | | |
|---|---|---|---|
| 3,528,888 | 9/1970 | Deutsch | 435/26 |
| 3,539,453 | 11/1970 | Deutsch | 435/26 |
| 3,867,258 | 2/1975 | Forgione | 435/26 |
| 3,957,584 | 5/1976 | Kronish et al. | 435/805 |

*Primary Examiner*—Esther M. Kepplinger
*Attorney, Agent, or Firm*—Bruce D. Sunstein

[57] ABSTRACT

A test indicator determines concentration, in a biological fluid, of a metabolic acid, such as beta-hydroxybutyrate or lactic acid. The indicator includes a test surface containing the dried residue resulting from impregnation of the surface with components including a tetrazolium salt, nicotinamide adenine dinucleotide (NAD), an electron carrier, and the enzyme that is a dehydrogenase for the specific metabolic acid being assayed. The indicator also includes a physically distinct provision for buffering the reaction. In accordance with the concentration of the metabolic acid being assayed, the indicator provides a predetermined color or intensity which can be observed either with the naked eye or with instrumentation such as a reflectance meter.

16 Claims, No Drawings

SEMI-QUANTITATIVE ASSAY OF METABOLIC ACIDS

BACKGROUND OF THE INVENTION

This application is a continuation-in-part of my application, Ser. No. 925,946, filed July 19, 1978, issuing as U.S. Pat. No. 4,254,222.

The present invention relates to determination of the concentration of specific metabolic acids in biological fluids, and in particular, the concentration of betahydroxybutyrate and lactic acid in biological fluids.

In humans, as well as in certain other animals, the organism may experience or suffer from a state of metabolic acidosis. Of the types of acidosis, there are recognized hyperketonemia, hyperlacticacidemia, uremicacidemia, and toxicacidemia.

On certain occasions, it may be possible to determine that there is present a condition of metabolic acidosis, but determination of the type of acidosis present may be difficult without expensive and time-consuming laboratory analysis. Moreover, it may be difficult to determine even whether there is present a metabolic acidosis condition. For example, with respect to hyperketonemia there is a rapid semiquantitative test for only one ketone body, namely, acetoacetate. The test for acetoacetate concentration is made by use of a nitroprusside impregnated test surface. The test surface is then immersed in the biological fluid to be assayed, and an indication of the concentration can be obtained by observing the color of the test surface after a predetermined time has elapsed. Disadvantages of the nitroprusside technique are discussed in K. G. M. M. Alberti and T. D. R. Hockaday, "Rapid Blood Ketone Body Estimation in the Diagnosis of Diabetic Ketoacidosis," 1972 British Medical Journal, 2, 565–568. The nitroprusside technique does not measure the concentration of betahydroxybutyrate, the major ketone body. The result is the possibility of a misleading determination of the total ketone bodies in the biological fluids.

Although lactic acidosis may be the most common form of metabolic acidosis, there is a problem in determining rapidly the concentration of lactate in biological fluids. Short of laboratory analysis, it is common for the physician to assume the presence of lactic acidosis when other forms of metabolic acidosis have been ruled out by other techniques. For example, the relatively poor nitroprusside technique is used to rule out the presence of hyperketonemia, and other methods are used to rule out the presence of uremicacidemia and toxicacidemia. Thus, despite the frequency of occurrence of lactic acidosis, the number of cases actually documented on the basis of direct analysis are relatively uncommon.

SUMMARY OF THE INVENTION

The invention provides a test indicator for determining the concentration, in a biological fluid, of a metabolic acid, such as beta-hydroxybutyrate or lactic acid. The indicator includes a test surface containing the dried residue resulting form impregnation of the surface with components including a tetrazolium salt, nicotinamide adenine dinucleotide (NAD), an electron carrier, and the enzyme that is a dehydrogenase for the specific metabolic acid being assayed. The indicator also includes a physically distinct provision for buffering the reaction. In accordance with the concentration of the metabolic acid being assayed, the indicator provides a predetermined color or intensity which can be observed either with the naked eye or with instrumentation such as a reflectance meter. In accordance with the present inventions test reagents were concentrated and applied to inert test surfaces in sufficient quantities so that they could react with specific substrates, beta-hydroxybutyrate or lactate, in a quantitative manner.

DESCRIPTION OF SPECIFIC EMBODIMENTS

The invention assays the concentration of a metabolic acid by oxidizing the acid enzymatically with a corresponding reduction of nicotinamide adenine dinucleotide (NAD) to NADH. The NADH that has been formed is ineffective in reducing directly a tetrazolium salt to a formazan. Consequently an intermediate electron carrier is used, such as 8-dimethylamino-2,3-benzophenoxazine (meldola blue). Reactions then following are the oxidation of NADH back to NAD by the meldola blue. The reduced meldola blue is then capable of reducing the tetrazolium salt to its colored formazan. A suitable tetrazolium salt is 2-p-iodophenyl-3-(p-nitrophenyl)-5-phenyltetrazolium chloride (INT).

I have found that the above reaction cannot be used straightforwardly to make a dry test indicator for determining metabolic acid concentration. In view of the above reaction one may speculate that an absorbant paper could be immersed in a solution of the metabolic acid dehydrogenase with NAD, electron carrier, and the tetrazolium salt. The paper, after being dried, could be immersed in the biological fluid under test, and its color there upon could, it would seem, be read as indicative of metabolic acid concentration.

This has not proved to be the case. The reaction should be buffered to make the indicator reliable, but I have found that hydration of an anhydrous buffer residue deposited on the absorbant paper can give rise to false readings. Consequently, the buffer is provided separately from the anhydrous residue of enzyme, NAD, electron carrier, and tetrazolium salt. I have, moreover, found that the reduction of the tetrazolium salt to its colored formazan is enhanced by use of a catalyst such as potassium palladium tetrachloride, and this catalyst is included in the solution in which the absorbant paper is immersed, so that it is included in the residue on the paper after the paper is dried.

As used in the claims, the term "test surface" is meant to include any suitable paper or equivalent structure, for making a test indicator, in accordance with methods known in the art.

EXAMPLE 1

BOHB Assay

An enzyme-reagent solution is made with components in the following concentrations:

(1) beta-hydroxybutyric acid dehydrogenase 60 I.U./ml;
(2) enzyme cofactor beta-nicotinamide adenine dinucleotide (beta-NAD) 21 mM;
(3) electron carrier 8-dimethylamino-2,3-benzophenoxazine (meldola blue) 0.25 mM;
(4) tetrazolium salt 2-(p-iodophenyl)-3-(p-nitrophenyl)-5-phenyl tetrazolium chloride (INT) 8.9 mM;
(5) tetrazolium reduction catalyst potassium palladium tetrachloride ($K_2PdCl_4$) 0.10 mM;
(6) formazan solubilizer isooctylphenoxypolyethoxyethanol (Triton x-100) 1% v/v.

The solution is then evenly distributed on a light yellow, thin, absorbent paper, which, in turn, is dried in a desiccated vacuum.

Another impregnated paper must also be prepared to afford the desired pH for the reaction to take place. Eaton Dikeman paper #204, a thick paper, is saturated with an equal volume mixture of two buffers and dried. These buffers are prepared by adjusting a 1 M glycine solution to a pH of 8.8 with sodium hydroxide and by adjusting a 1 M potassium monohydrogen phosphate solution with potassium dihydrogen phosphate to pH of 8.8. The paired-buffer solution is evenly distributed over this second paper, which is also dried in a desiccated vacuum. The paired-buffer paper is placed under the enzyme-reagent impregnated paper and the two papers are stored and used together as a package unit.

Applying the biological fluid with the unknown quantity of betahydroxybutyrate to "dry" inert surfaces of the impregnated and layered papers causes color changes proportional to the amount of betahydroxybutyrate present in the biological fluid. Colors vary from light blue-gray, corresponding to zero concentration; very pale-pink, corresponding to a trace; a light-pink, corresponding to a 1.0–2.5 mM concentration; light-red, corresponding to 2.5–5.0 mM concentration; and deep-red, corresponding to 7.5–10.0 mM and greater concentrations. The test result is compared to a specific color chart two minutes after applying the biological fluid, and appropriate quantifications are made.

EXAMPLE 2

Lactic Acid Assay

An enzyme reagent solution is made with components as in Example 1, except that lactic acid dehydrogenase, 2750 I.U./ml is substituted for component (1) of that example. As in Example 1, the solution is then evenly distributed on a light yellow, thin, absorbent paper, which, in turn, is dried in a desiccated vacuum.

For the buffer-paper, Eaton Dikeman paper #204 is saturated with a 1.0 M glycine solution that has been djusted to a pH of 9.5 with sodium hydrozide. The buffer solution is evenly distributed over this second paper, which is also dried in a desiccated vacuum. The buffer paper is placed under the enzyme-reagent impregnated paper and the two papers are stored and used together as a package unit.

Applying the biological fluid with the unknown quantity of lactate to "dry" inert surfaces of the impregnated and layered papers causes color changes proportional to the amount of lactate present in the biological fluid. Concentration of lactate is measured in accordance with the same color-concentration list given in Example 1.

Accordingly, while the inventin has been described with particular reference to specific embodiments thereof, it will be understood that it may be embodied in a variety of forms diverse from those shown and described without departing from the spirit and scope of the invention as defined by the following claims.

What is claimed is:

1. A test indicator for determining the concentration of a metabolic acid selected from the group consisting of beta-hydroxybutyrate and lactic acid in a biological fluid, such indicator comprising:
   (a) a first absorbant test surface containing the dried residue resulting from impregnation of the surface with components including
   (i) a tetrazolium salt;
   (ii) nicotinamide adenine dinucleotide (NAD);
   (iii) an electron carrier;
   (iv) the enzyme that is a dehydrogenase for the metabolic acid; and
   (b) means, distinct from the first absorbant test surface, for buffering the biological fluid, wherein said recited components are present in amounts sufficient to react together to determine the concentration of said acid.

2. A test indicator according to claim 1, wherein the means for buffering the biological fluid comprises a second absorbant test surface, proximate to the first test surface, containing the dried residue resulting from impregnation of the surface with a buffer solution.

3. A test indicator according to claim 2, wherein the metabolic acid is beta-hydroxybutyrate (BOHB), and the enzyme is BOHB dehydrogenase.

4. A test indicator according to claim 3, wherein the first test surface contains the dried residue resulting from impregnation of the surface with components also including potassium palladium tetrachloride.

5. A test indicator according to claim 4, wherein the electron carrier is 8-dimethylamino-2,3-benzophenoxazine (meldola blue).

6. A test indicator according to claim 5, wherein the first test surface contains the dried residue resulting from impregnation of the surface with components also including formazan solubilizer alkylphenoxypolyethoxyethanol, and wherein the tetrazolium salt is 2-(p-iodophenyl)-3-(p-nitrophenyl)-5-phenyl-2H tetrazolium chloride (INT).

7. A test indicator according to claim 5, wherein the buffer solution is at a pH of approximately 8.8.

8. A test indicator according to claim 7, wherein the first test surface contains the dried residue resulting from impregnation of the surface with components having approximately the same relative proportions as the following concentrations per unit volume:
   INT, 8.9 mM
   NAD, 21 mM
   Meldola blue, 0.25 mM
   BOHB dehydrogenase, 60 I.U./ml.
   potassium palladium tetrachloride, 0.10 mM
   alkylphenoxypolyethoxyethanol, 1% v/v 9. A test indicator according to claim 7, wherein the buffer solution includes (a) glycine buffered with sodium hydroxide at a pH of approximately 8.8 and (b) potassium dihydrogen phosphate buffered with potassium dihydrogen phosphate at a pH of approximately 8.8.

10. A test indicator according to claim 2, wherein the metabolic acid is lactic acid and the enzyme is lactic dehydrogenase.

11. A test indicator according to claim 10, wherein the first test surface contains the dried residue resulting from impregnation of the surface with components also including potassium palladium tetrachloride.

12. A test indicator according to claim 11, wherein the electron carrier is 8-dimethylamino-2,3-benzophenoxazine (meldola blue).

13. A test indicator according to claim 13, wherein the first test surface contains the dried residue resulting from impregnation of the surface with components also including formazan solubilizer alkylphenoxypolyethoxyethanol, and wherein the tetrazolium salt is 2-(p-iodophenyl)-3-(p-nitrophenyl)-5-phenyl-2H tetrazolium chloride (INT).

14. A test indicator according to claim 13, wherein the buffer solution is at a pH of approximately 9.5.

15. A test indicator according to claim 14, wherein the first test surface contains the dried residue resulting from impregnation of the surface with components having approximately the same relative proportions as the following concentrations per unit volume:
INT, 8.9 mM
NAD, 21 mM
Melodola blue, 0.25 mM
lactic dehydrogenase, 2750 I.U./ml
potassium palladium tetrachloride, 0.10 mM
alkyl phenoxypolyethoxyethanol, 1% v/v 16. A test indicator according to claim 15, wherein the buffer solution includes glycine buffered with sodium hydroxide at a pH of approximately 9.5.

* * * * *